(12) United States Patent
Lim

(10) Patent No.: US 9,526,426 B1
(45) Date of Patent: Dec. 27, 2016

(54) APPARATUS AND METHOD FOR ASSESSING TISSUE COMPOSITION

(71) Applicant: Bernard Boon Chye Lim, Springfield, IL (US)

(72) Inventor: Bernard Boon Chye Lim, Springfield, IL (US)

( * ) Notice: Subject to any disclaimer, the term of this patent is extended or adjusted under 35 U.S.C. 154(b) by 558 days.

(21) Appl. No.: 13/945,749

(22) Filed: Jul. 18, 2013

Related U.S. Application Data

(60) Provisional application No. 61/673,025, filed on Jul. 18, 2012.

(51) Int. Cl.
*A61B 5/00* (2006.01)
*A61B 19/00* (2006.01)

(52) U.S. Cl.
CPC .......... *A61B 5/0075* (2013.01); *A61B 5/0073* (2013.01); *A61B 19/5244* (2013.01)

(58) Field of Classification Search
CPC .. A61B 5/0075; A61B 5/0073; A61B 19/5244
USPC .................................. 600/473–480; 606/41
See application file for complete search history.

(56) References Cited

U.S. PATENT DOCUMENTS

| | | | |
|---|---|---|---|
| 4,830,014 A | 5/1989 | Goodman et al. | |
| 5,041,109 A | 8/1991 | Abela | |
| 5,298,026 A | 3/1994 | Chang | |
| 5,643,251 A | 7/1997 | Hillsman et al. | |
| 5,647,870 A | 7/1997 | Kordis et al. | |
| 5,651,785 A | 7/1997 | Abela et al. | |
| 5,693,043 A | 12/1997 | Kittrell et al. | |
| 5,762,609 A | 6/1998 | Benaron et al. | |
| 5,904,651 A * | 5/1999 | Swanson | A61B 5/0084 600/342 |
| 6,178,346 B1 | 1/2001 | Amundson et al. | |
| 6,219,566 B1 | 4/2001 | Weersink et al. | |
| 6,690,966 B1 | 2/2004 | Rava et al. | |
| 7,232,437 B2 | 6/2007 | Berman et al. | |
| 7,238,180 B2 | 7/2007 | Mester et al. | |
| 7,255,695 B2 | 8/2007 | Falwell et al. | |
| 7,662,152 B2 | 2/2010 | Sharareh et al. | |
| 7,850,685 B2 * | 12/2010 | Kunis | A61B 18/1492 606/41 |
| 7,952,719 B2 | 5/2011 | Brennan | |
| 8,048,063 B2 | 11/2011 | Aeby et al. | |
| 8,052,605 B2 | 11/2011 | Muller et al. | |
| 8,078,268 B2 | 12/2011 | Maier et al. | |
| 8,182,433 B2 | 5/2012 | Leo et al. | |
| 8,500,730 B2 | 8/2013 | Lee et al. | |
| 8,628,520 B2 | 1/2014 | Sharareh et al. | |

(Continued)

OTHER PUBLICATIONS

Pearce JA., Proceedings of the SPIE, Feb. 2009, pp. 718104-1 to 718104-15, vol. 7181 (see p. 718104-1 to 718104-6)Soc. Optics and Photonics, US.

(Continued)

*Primary Examiner* — Sanjay Cattungal
(74) *Attorney, Agent, or Firm* — John M. Berns

(57) ABSTRACT

A tissue composition monitoring apparatus that includes a catheter with an optical sensor for tissue composition monitoring and ablation lesion determination via an automated algorithm incorporating Arrhenius model thermal denaturation kinetics for determining the characteristics of tissue for example the transmurality of the ablation lesion.

45 Claims, 14 Drawing Sheets

(56) References Cited

U.S. PATENT DOCUMENTS

| | | | |
|---|---|---|---|
| 8,712,550 B2* | 4/2014 | Grunewald | A61B 18/1492 600/381 |
| 8,842,953 B2 | 9/2014 | Mihajlovic et al. | |
| 2006/0229515 A1 | 10/2006 | Sharareh et al. | |
| 2008/0125634 A1 | 5/2008 | Ryan et al. | |
| 2008/0287942 A1 | 11/2008 | Amundson | |
| 2010/0063492 A1 | 3/2010 | Kahlert | |
| 2010/0317974 A1 | 12/2010 | Alfano et al. | |
| 2011/0190760 A1 | 8/2011 | Niver et al. | |
| 2013/0204134 A1 | 8/2013 | Harks et al. | |

OTHER PUBLICATIONS

Agah, R et al., IEEE Transactions on Biomedicai Engineering, Aug. 1996, pp. 839-846, vol. 43 No. 8, (see p. 842-844) Inst. Eiect. & Electronics US.

Yun SH et al., Optics Express, Jun. 2004, pp. 2977 to 2998, vol. 12 No. 13 (see p. 2978) The optical Soc. US.

Erdemir, A. et al., Journal of Biomechanics, Mar. 2003, pp. 449-455, vol. 36 No. 3 (see p. 449-455) Am. Soc. Biomechanics US.

Lindbergh T "Quantitative Diffuse Reflectance Spectroscopy" 2009 (see p. 62).

Chin LCL et al., pp. 678-688, Optical-Thermal Response of Laser-Irradiated Tissue, 2nd ed., pp. 337-338, A.J. Welch, M.J.C. van Gernert (eds.).

Kuck et.al, Heart Rhythm Journal, Jan. 2012, pp. 18-23, vol. 9 No. 1 (see p. 18-23) Heart Rhythm Soc. USA.

Barton J., pp. 337-338, Optical-Thermal Response of Laser-irradiated Tissue, 2nd ed., , A.J. Welch, M.J.C. van Gemert (eds.), Springer, Netherlands. 2011 (see p. 337-338).

Ouyang F et. al., Circulation, Jan. 2005, pp. 127-135, vol. 111, No. 2 (see p. 129-135) AmericanHeart Assoc. US.

Ranjan R et al., Circulation: Arrhythmia and Electrophysiology, Jun. 2011, pp. 279-286, vol. 4 No. 3 (see p. 282-285) American Heart Assoc. US.

Ranjan R et al., Circulation: Arrhythmia and Electrophysiology, Jun. 2011, pp. 279-286, vol. 4 No. 3 (see p. 282-285) AHA, USA.

Melby SJ et al., Heart Rhythm Journal, Sep. 2008, pp. 1296-1301, vol. 5 No. 9 (see p. 4-6) Heart Rhythm Soc. USA.

Cui W et al., Proceeedings of the SPIE , May 1991; pp. 180-191, vol. 1431. (see p. 180-191) Soc. Optics and Photonics, USA.

Davis M et al., Journal of the American College of Cardiology Jul. 2013, pp. 231-241, vol. 62 No. 3 (see p. 231-241).

Ho S et al., Journal of Cardiovascular Electrophysiology , Nov. 1999, pp. 1525-1533, vol. 10, No. 11. (see p. 1526-1529) Wiley USA.

Atherton D et al., , Clinical Anatomy, Jul. 2012, pp. 628-633 vol. 25 No. 5 (see p. 629-631) Wiley USA.

Beauvoit B et al., Biophysical Journal, Dec. 1994, pp. 2501-2510. vol. 67 (see p. 2503-2509).

Thomsen S et al., Proceedings of the SPIE , Jun. 1990, pp. 2-11, vol. 1202 (see p. 2-11) Soc. Optics and Photonios, USA.

Clark III C at al., Journal of Biomedical Optics, Feb. 2011, pp. 020504-1 to 020504-3, vol. 16 No. 2 (see p. 020504-1 to 020504-3) (SPIE).

Bays R et al., Proceedings of the SPIE , Nov. 1991, pp. 397-408, vol. 1525. (see p. 401-407) Soc. Optics and Photonics, USA.

* cited by examiner

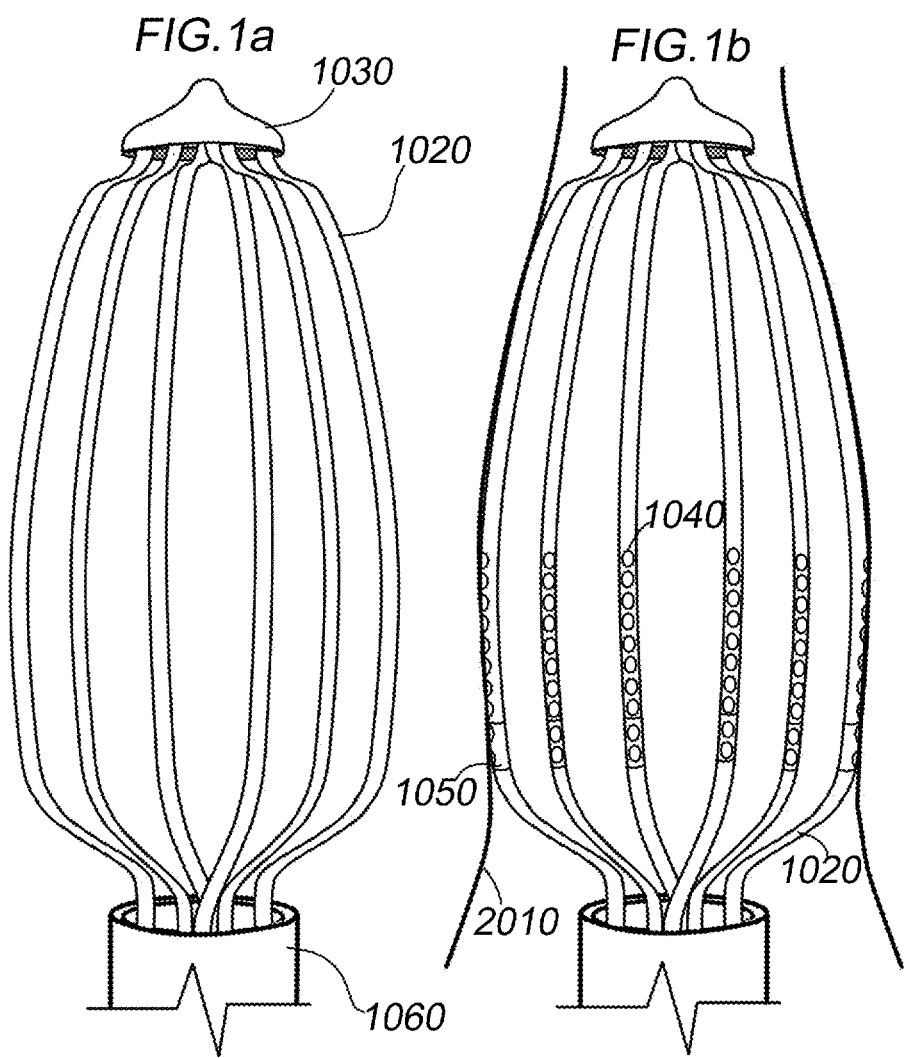

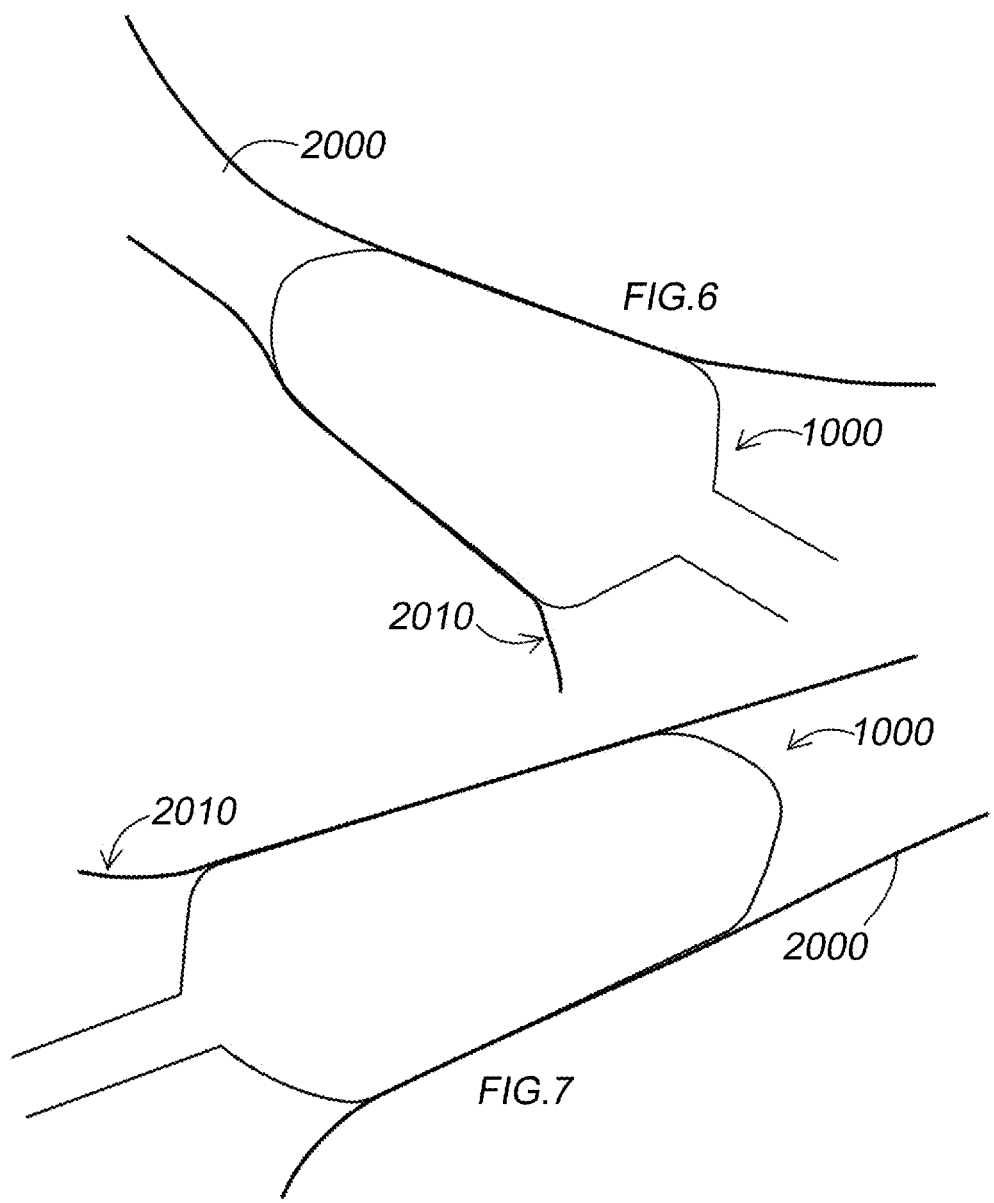

APPARATUS AND METHOD FOR ASSESSING TISSUE COMPOSITION

This Application Claims the benefit of U.S. Provisional Patent Application No. 61/673,025 filed Jul. 18, 2012 and titled SYSTEMS AND METHODS FOR IMPROVING EFFICACY AND SAFETY IN ABLATION PROCEDURES

FIELD OF THE INVENTION

The invention relates to a tissue composition monitoring apparatus, a tissue composition monitoring method and an ablation lesion determination automated algorithm incorporating Arrhenius model thermal denaturation kinetics for determining the characteristics of tissue for example the transmurality of the ablation lesion.

BACKGROUND OF THE INVENTION

Methods incorporating diffuse reflectance spectroscopy (DRS), into standard ablation catheters suffer from instability of collection of optical spectra due to motion of the catheter and inconsistent contact pressure. Furthermore, DRS deployed with a small offset between illuminating and collecting fibers have only small penetration depths. Standard ablation catheters cannot achieve a sufficient spatial offset between illuminating and receiving optic fibers due to the limited length of the distal tip of the ablation catheter that is in contact with the heart during ablation and therefore cannot exploit spatial offset to achieve greater penetration depths.

In ablation of cardiac tissue, the "first hit" is the most important. Therefore applying energy in the correct dosage and for the correct duration is critical to achieving transmurality. Insufficient energy and duration will lead to ineffective lesions which result in local tissue swelling and edema which will prevent further effective completion of the lesion at the same location. Checking for lesion characteristics after the first ablation is therefore ineffective. On the other hand, applying too much energy for too long can lead to collateral damage like coagulum formation and damage to surrounding structures. What is therefore needed is a device and method to allow monitoring of the ablation lesion as it is being formed and to adjust power and duration settings according to predetermined optimum levels for achieving transmurality and for preventing collateral damage.

DESCRIPTION OF RELATED ART

Systems which measure ablation lesions are known in the art. To quantify optical sensing data in a beating heart is challenging. There is substantial movement of the catheter. The translation of the catheter can be by as much as 1 cm within the timeframe of a single heartbeat. This movement can lead to significant error in spectrophotometer readings and even ultrasound images.

Harks et al., (WO 2012/049621 A1), hereinafter "Harks," incorporates optic fiber within a standard ablation catheter that is subject to cardiac motion which can lead to significant errors in spectrophotometer readings and is subject to different contact pressures which can lead to significant errors in spectrophotometer readings. Furthermore, in moving past catheters around the cardiac atria there is a wide variation in the amount of pressure applied to the tissue. Kuck et. al; A novel radiofrequency ablation catheter using contact force sensing: Toccata study. Heart Rhythm 2012 January; 9(1): 18-23 hereinafter "Kuck," shows that there exists large inter-individual and intra-individual variability in contact pressure of the ablation catheter within the left atrium. Even within a single individual, there is a wide variability in contact pressure as the catheter is moved from point to point in the heart which can differ by as much as up to 40 g as the ablation catheter is moved around the pulmonary veins. In addition, depending in the individual clinician performing the ablation, a large variation in contact force up to 60 g is possible Irrespective of the source, variability in pressure against tissues can influence measurement of optical sensing data. Variations in pressure on tissue can lead to variations in scattering and absorbance coefficients by as much as up to 25% due to extrusion of water from tissue.

Accordingly, a preferred embodiment according to the present invention provides a stable platform having a basket shape with distal splines "hugging" the inside of the pulmonary vein and with the conical part of the basket "straddling" the os of the pulmonary vein and providing a stable contact pressure (FIGS. 1a and 1b).

With past ablation systems such as those used for atrial fibrillation and ventricular tachycardia, there is no method of checking for transmurality so that there is a significant variation in power delivery and duration of power delivery between different operators. As a result of this, there is a significant recurrence rate of arrhythmias, between 30 to 50 percent for atrial fibrillation. For ventricular tachycardia, the recurrence rate is even higher because ventricular tissue is thicker and so it is harder to achieve transmurality.

Studies have shown that when inpatients come back with recurrence of atrial fibrillation, the pulmonary veins typically have reconnected, proving the inability of current ablation systems to achieve transmurality.

Histology studies have shown that a rim of unablated tissue as little as 1.4 mm can lead to reconnection of pulmonary veins and lead to recurrence of atrial fibrillation.

In ablation catheters adapted for renal denervation where the sympathetic nerves on the surface of the renal artery are the targets for ablation, there is currently no endpoint for ablation. As such, the operator is not able to discern when the nerves have been ablated. As such there have been reports of thrombus formation and even dissection of the renal artery, due perhaps to delivery too much power for too long. Accordingly, It would be desirable to provide a system that is configured to interrogate deeper layers of tissue to select out the layer of tissue for ablation and to observe for transmurality with NIR spectroscopy that can provide a constant contact force and also reduce the effect of the beating motion of the heart. To achieve this, diffuse reflectance spectroscopy must be configured to be able to pick up the deeper layers of tissue. Spatially offset diffuse reflectance spectroscopy (SODRS), where there is a spatial offset between the illumination and the receiving optic fibers will allow NIR interrogation of the deeper layers of tissue.

Cui at al have shown that the path of photon travel through tissue is "banana shaped" so that the depth of tissue interrogated will be approximately half the distance of the spatial offset. Cui, W, Kumar, C. and Chance, B. (1991) *Experimental study of migration depth for the photons measured at sample surface. I. Time resolved spectroscopy and imaging. Proc. SPIE Int. Soc. Opt. Eng.* 1431, 180±191. Because depth of the muscle layer in the left atrium can range from up to a maximum of 5 mm, a spatial offset of 10 mm is required to optically interrogate the deepest layer of muscle in the left atrium. The intimal layer of the renal artery can be up to to 6 or 7 mm thick. Renal denervation targets the sympathetic nerves that lie within the layer of adventitial fat which is another 2 mm thick. Therefore for renal denervation, an offset of 20 mm may be required. For ventricular tachycardia ablation, the tissue to be ablated is thicker. Therefore a bigger spatial offset of 30 to 35 mm between the illuminating and receiving fibers will be required. This can be offset by being able to use a basket with a relatively larger diameter in the larger cavity of the ventricle.

The geometry of standard ablation catheters does not permit a wide spatial offset between illuminating and receiving optic fibers positioned at the distal tip that is required to truly achieve analysis of transmurality for the reason that typically, only between 3 to 4 mm of the distal tip of the catheter is in contact with the muscle tissue. It is difficult to ensure a constant end-on or side-on contact of standard ablation catheters with the tissue surface. Furthermore, the systems of the prior art typically have a spatial offset of 1.7 mm which means that it is only interrogating the superficial tissue layers of 0.4 to 0.8 mm.

SUMMARY OF THE INVENTION

In one aspect of the present invention, a tissue composition monitoring apparatus, an ablation lesion monitoring method and an ablation lesion determination automated algorithm incorporates Arrhenius's model for thermal denaturation kinetics for determining the characteristics of the ablation lesion. The apparatus includes a basket catheter configuration for achieving stability and consistent contact pressure during ablation for collection of optical spectra. The basket catheter incorporates a linear portion which "hugs" the conical portion of the pulmonary vein during atrial fibrillation ablation and allows a variable spatial offset of between 10 mm to 20 mm between the illuminating optic fiber and the receiving optic fiber.

One embodiment according to the present invention is adapted for renal denervation whereby the diameter of the basket is 4 mm and the spatial offset can range from 8 mm to 20 mm due to the fact that the longer horizontal; i.e., more tubular geometry, of the renal artery can allow for a longer linear segment of the basket catheter to "abut" the inner lumen of the renal artery (FIG. 2). The basket catheter is delivered to the target site in a "collapsed" configuration within a sheath.

For atrial fibrillation ablation, the sheath is placed within the pulmonary vein under fluoroscopic guidance and the sheath is withdrawn, which allows the basket to assume its preformed shape which will then "abut" the inside of the pulmonary vein (FIG. 3). The basket is slowly withdrawn until the wider part of the basket "pops out" of the vein and "abuts" the conical part of the vein. The narrow part of the basket will stay inside the vein and help to stabilize the catheter whereas the wider part will provide a linear stretch of 10 mm of apertures for performing spatially offset diffuse reflectance near infrared spectroscopy.

For renal denervation, the sheath is deflected into the os of the renal artery and the basket catheter is deployed into the renal artery, with the expanded basket catheter abutting the inner lumen of the renal artery. An optical sensor comprising a plurality of splines each containing optical fibers with the illuminating and collecting fibers spatially offset to achieve greater penetration depth.

It is preferred that the apparatus is in the form of a catheter with the distal end comprising a basket configuration. The catheter can be introduced into a person or an animal by means of a sheath and when in the desired organ, for example the heart, the sheath can be directed into the pulmonary vein, the sheath withdrawn and the basket configuration allowed to expand within the vein, thus maintaining stability for optical spectra collection.

It is preferred that the apparatus comprises an energy delivery element for delivering of energy to tissue. The energy delivery element is preferably integrated with the catheter together with optical elements. Tissue characteristics can be determined before energy is applied and during application of energy.

The energy delivery element can be a radiofrequency electrode for applying RF energy. However, other types of energy may be used, for example laser ablation, cryoablation.

The optical sensor element comprises a basket catheter with a plurality of splines containing a plurality of optic fibers. One of the optic fibers is for illuminating and the other optic fiber is for collection. The illuminating fibers and the optic fibers are spatially offset from each other to achieve greater depth penetration in order to assess the characteristics of the tissue for example transmurality of the ablation lesion. The illuminating optic fibers are connected to a light source like a laser and the optic fibers guide the light to the tissue. The collection fibers are preferably connected to a spectrophotometer for generating optic spectra of the tissue wherein the invention is adapted to determine the characteristics of the tissue for example transmurality of the ablation lesion depending on the characteristics of the optic spectra.

It is preferred that the invention is adapted to determine the transmurality of the ablation lesion from the optical sensing data. The optical sensing data are indicative of the absorption and scattering properties of the tissue. The invention can therefore be adapted to assess the transmurality of an ablation lesion and/or the composition of the tissue based on the optical sensing data.

In a preferred embodiment, the invention comprises computer memory in which the optical spectra are stored, which are assigned to ablated tissue with 100% transmurality.

The invention is also preferably adapted to compare the stored (known) spectra with actually measured spectra in order to differentiate between muscle and fibrosis (collagen), between fat and muscle, between fat and nervous tissue in addition to the transmurality of ablated tissue.

The invention can comprise a memory in which optical spectra are stored which are assigned to different types of tissue for example, fat, muscle, collagen, nerve and water in which the invention can be adapted to determine the type of tissue by comparing the stored spectra with the actually measured optical spectra.

It is preferred that energy has been applied continuously for example, in a circle around the pulmonary veins in atrial fibrillation ablation. The invention is adapted to determine whether ablation has been carried out continuously along the circle depending on the optical sensing data. The basket configuration is adapted to deliver multiple ablation points simultaneously. This can achieve a "one-shot" ablation where due to the density of the splines, only one ablation is needed for a continuous circle around the pulmonary veins, or "2 or 3 shots" are required by rotating the basket clockwise and counterclockwise from the initial ablation location. 2 or 3 shots may be required in an embodiment where the density of the splines is kept for example to 8 splines/arms to reduce the stiffness of the basket (FIG. 1).

For renal denervation, the object is not to achieve a circumferential ablation around the renal artery in order to avoid stenosis of the artery. Instead, the object is to deliver ablation lesions in a spiral fashion along the long axis of the renal artery. Ablation can be carried out selectively to ablation electrode 1 and 5 and then catheter moved distally, then ablation is carried out at electrodes 2 and 7 and then catheter moved more distally, and ablation carried out at electrodes 3 and 8 etc.

The preferred embodiment will be perfused by fluid, through the apertures on the splines or through a central shaft.

The present invention is adapted to control the delivery of energy depending on the rate of change of the optical properties of the tissue. The rate of change of the optical properties of the tissue being ablated can be used to track the process of tissue denaturation. The rate of change of the optic properties of tissue can be fit to a curve with the exponential function I−exp(−t/r), which is modeled on Arrhenius equation for thermal denaturation, thus allowing the extraction of the rate constant from the slope of the curve at the point where 63 percent of the tissue is denatured. The point at which the rate of change of optical properties is zero is associated with 100% transmurality. The rate constants for the optimal thermal denaturation reaction where 100% transmurality is achieved with a temperature of 60 degrees Celsius for a duration of between 30 to 60 seconds is determined in in vivo and ex-vivo experiments using nitroblue tetrazolium (NBT), staining of tissue to determine viability and hence transmurality and is stored in the memory of the invention. Thus as energy is delivered, the rate of change of optical sensing data and the graph generated can be compared against stored graph and rate of the change (slope) and energy adjusted or titrated to achieve the desired rate or graph or slope.

It is preferred that the invention has a display unit for showing optical data and the percentage of transmurality and/or composition of the tissue.

The invention incorporates a computer program which includes a program code means for causing the invention as defined in claim 1 to carry out the steps of the ablation lesion assessment method as defined in claim when the computer program is run on a computer controlling the invention.

BRIEF DESCRIPTION OF THE DRAWINGS

FIGS. 1a, 1b show a catheter with a cone shaped basket configuration at the distal end adapted for atrial fibrillation ablation;

FIGS. 6 and 7 shows a basket closely hugging the contours of the vein;

DETAILED DESCRIPTION OF THE PREFERRED EMBODIMENTS

Reference Listing

Figure 1:
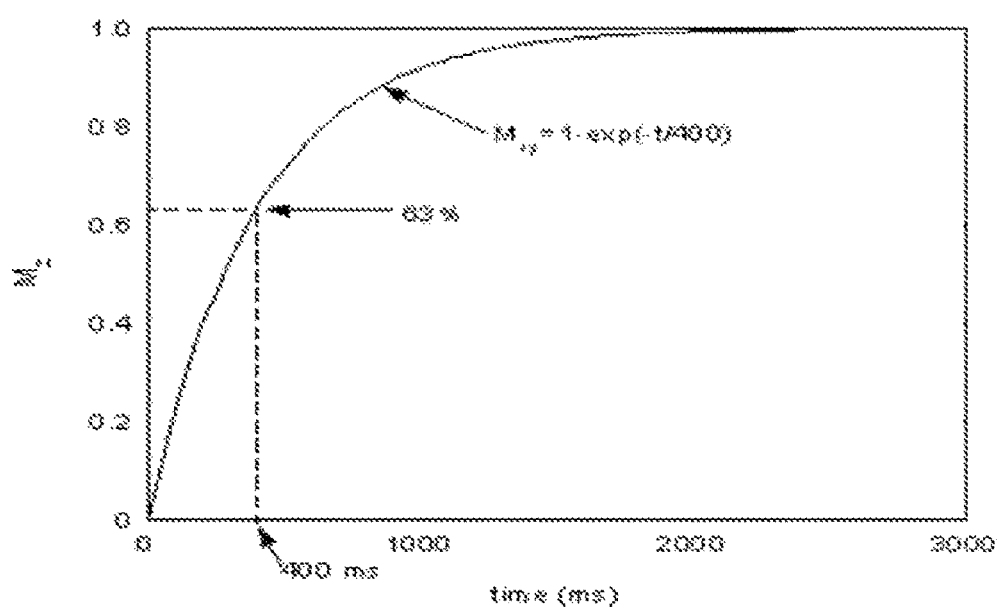
FIG. 1 is an exemplary Arrhenius equation.

1000 catheter
1010 optical sensor
1020 spline/arm
1024 photon path
1025 optic fiber
1027 receiving fiber
1028 illuminating fiber
1029 mirror
1030 cap
1040 aperture
1050 electrode
1051 wire to electrodes
1060 sheath
1070 basket
1080 MEMS gyroscope
2000 pulmonary vein
2010 opening pulmonary vein
2020 renal artery
2030 opening renal artery
3000 ablated tissue The present invention includes a catheter including optical sensors for generating optical sensing data that are indicative of the optical property of the tissue. FIG. 1 shows a preferred embodiment according to the present invention for determining the properties of a tissue. The distal end of catheter 1000 expands into a basket 1070 configuration with a plurality of arms or splines 1020.

Figure 4:
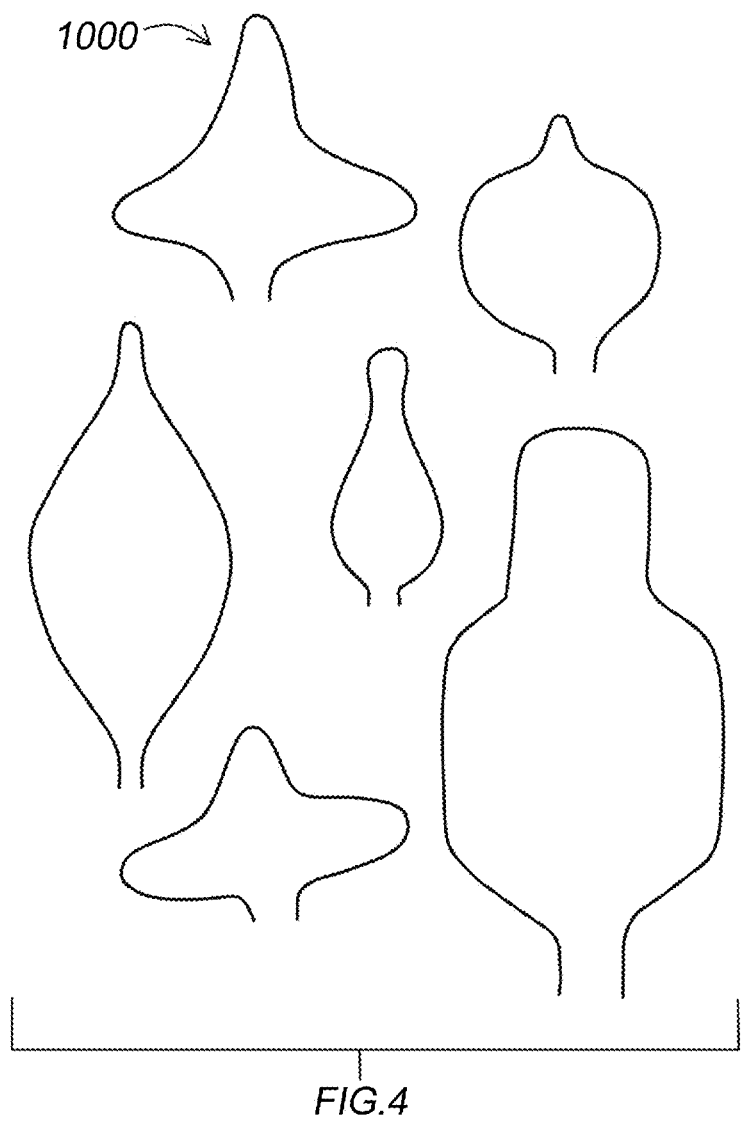
FIG. 4 shows a basket configuration with alternate shapes.

By way of non-limiting examples shown in FIG. 4, the basket can have a plurality of shapes. In a preferred embodiment, the basket has 8 splines or arms.

Figure 2:
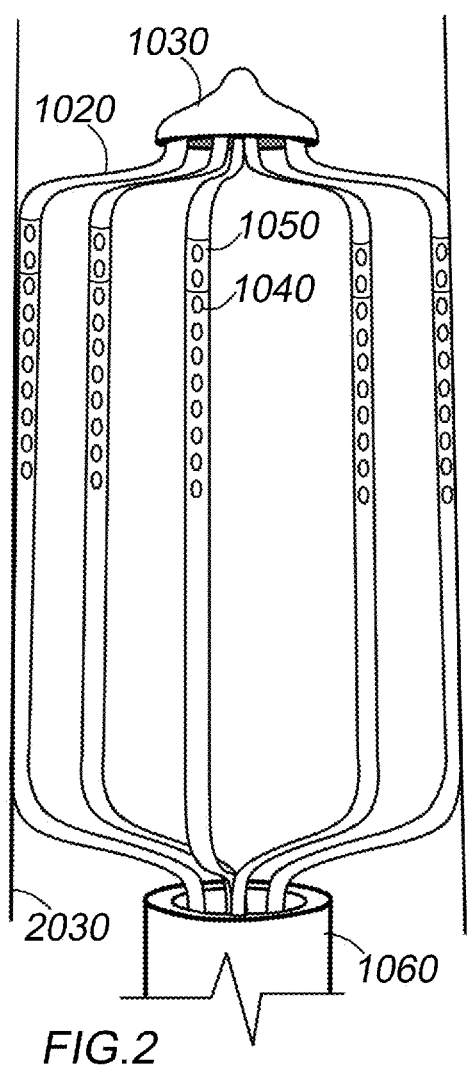
FIG. 2 depicts a catheter with a tubular basket configuration at the distal end adapted for renal denervation.
Figure 3:
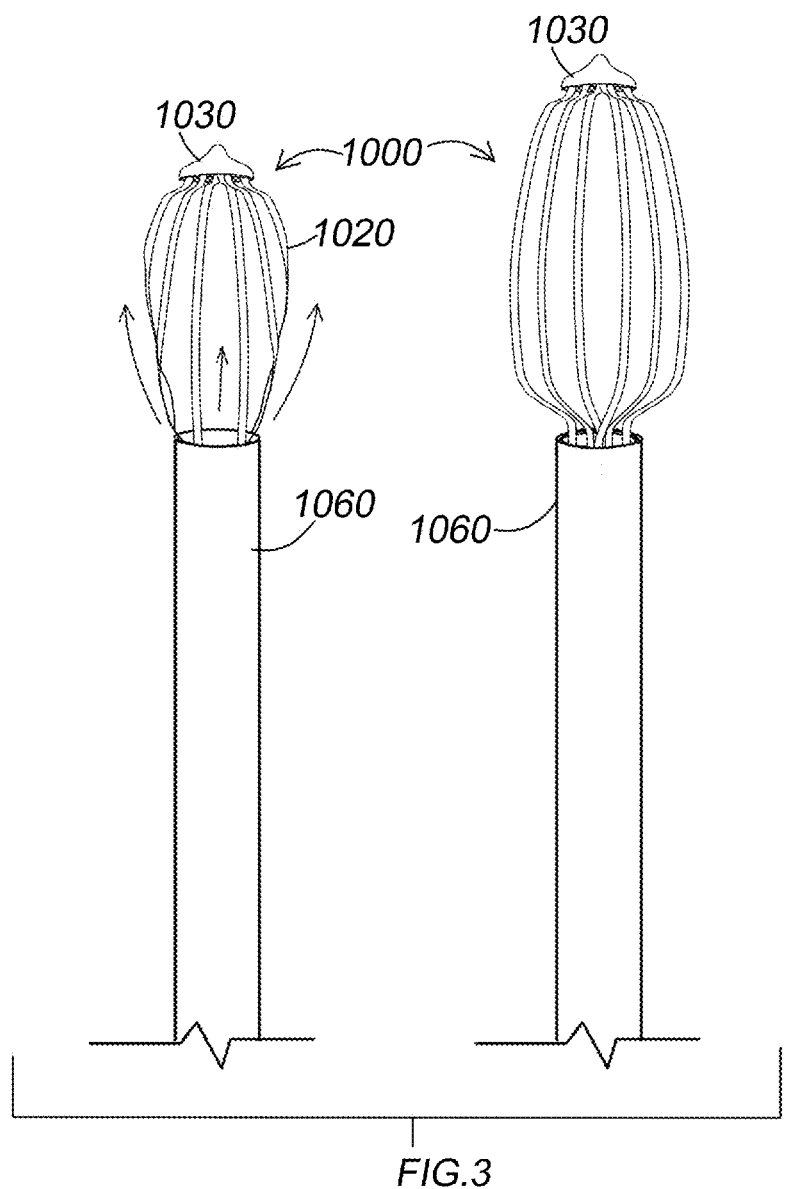
FIG. 3 shows a basket catheter delivered to the target site in a "collapsed" configuration within a sheath. The sheath is placed within the vessel (pulmonary vein or renal artery) under fluoroscopic guidance and the sheath is withdrawn, which allows the basket to assume its preformed shape which will then "abut" the inside of the vessel.

FIG. 2 shows the distal end of the catheter with the basket.

The distal end of each of arms 1020 is attached to a soft, non-traumatic cap 1030 and is preferably made of Pebax which has been doped with a radiopaque material like Barium Sulfate (FIGS. 1a and 1b).

The basket configuration can include wires, ribbons, cables and struts and can be constructed from either metals, non metals or combinations of both. The basket configuration can be coated with the Duraflo. Elements of the basket configuration can be made of one or more materials, including both metals and non metals. Typical metals chosen for basket construction include but is not limited to nitinol, stainless steel, elgiloy other alloys or any combinations thereof. The distal basket of the catheter has a preformed flexible shape which is designed to conform to the vessel in which the basket is placed. For atrial fibrillation ablation, the basket is shaped like a cone to "abut" the pulmonary vein.

A catheter 1000 includes a plurality of tubular components that can be steered by including a controllable pull wire at or near the distal end. Specifically, the catheter of the present invention can include an integral steering means, similar to existing catheters, such as a plurality of pull wires attached near a distal portion of the catheter and operably attached to a lever, knob or other control integral to a handle of the catheter. The steering mechanism is used to deflect the basket (used in conjunction with an outer sheath 1060 which may or may not be steerable) and distal end of the catheter into the left and right pulmonary veins of the left atrium. The integral catheter steering means can be used with a steerable transeptal sheath. A plurality of pull wires can be mounted 90 degrees apart at different locations in a distal portion of the catheter to provide multi-axis, precision controlled steering.

Figure 5:
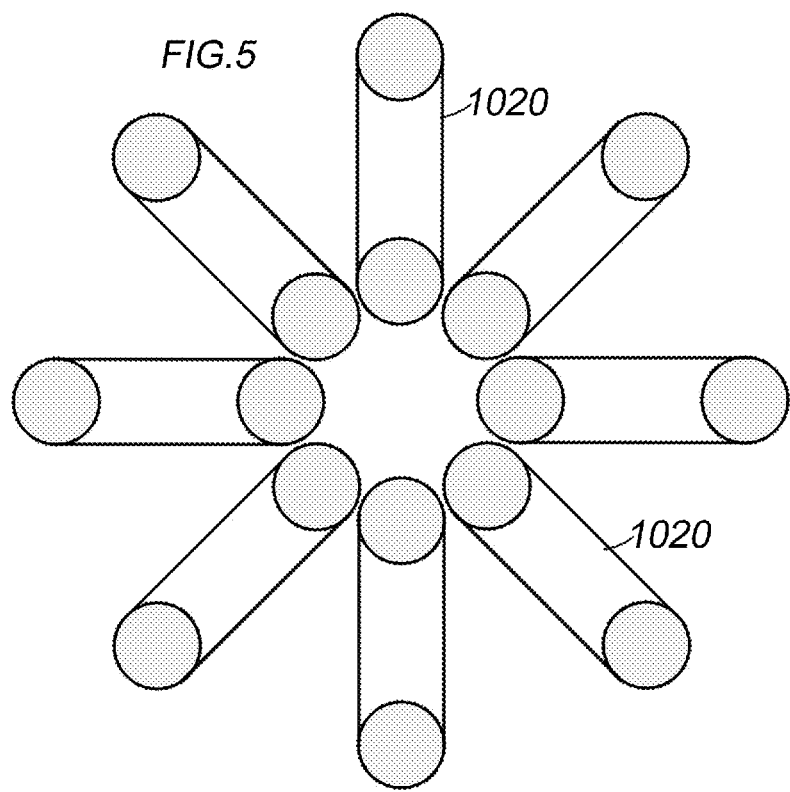
FIG. 5 is an end-on view of a basket according to a preferred embodiment of the present invention.
Figure 8:
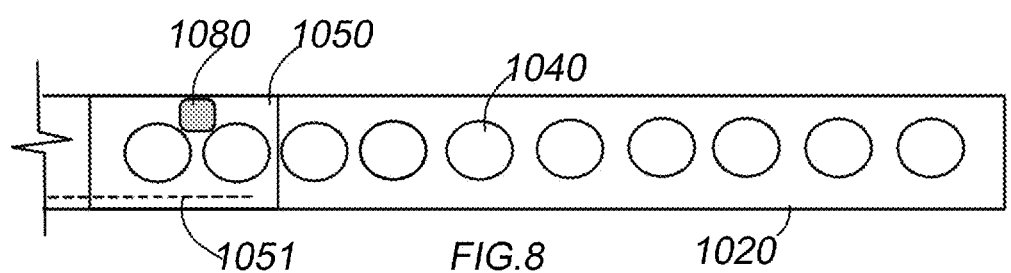
FIG. 8 depicts the structure of each nitinol spline tubing in the basket configuration for atrial fibrillation ablation.
Figure 9:
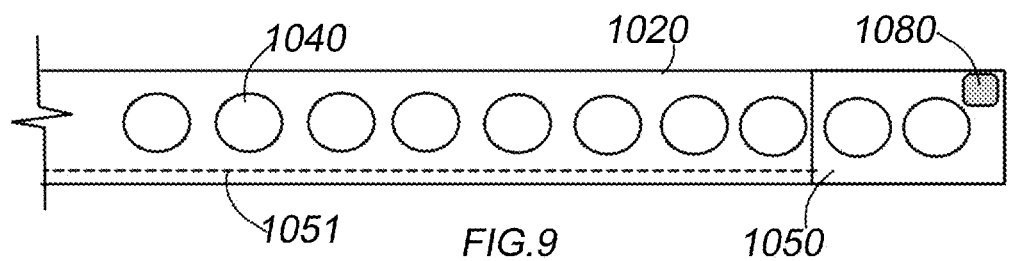
FIG. 9 depicts the structure of each nitinol spline tubing in the basket configuration for renal denervation.

Basket 1070 is introduced into the pulmonary vein via the deflectable sheath 1060 (for example the Agilus sheath, St Jude). The sheath is then withdrawn and the basket is allowed to expand fully to its preformed shape. FIG. 5 shows the end-on view of the basket. As seen in FIGS. 6 and 7, the basket will closely hug the contours of the vein. The basket is adapted to be deformable such that when the outer steerable sheath is withdrawn, the basket will expand to its maximum diameter to "abut" and press tightly against the conical portion of the pulmonary vein which extends from the os of the vein to approximately 20 mm into the vein. The basket is adapted with this linear segment of the basket designed with a series of drilled apertures 1040 measuring 300 micrometers each and separated by 760 micrometers enclosing optic fibers 1025 for performing spatial offset diffuse reflectance spectroscopy (FIGS. 8 and 9). Ensuring close contact between basket and tissue and critically maintaining stability and constant contact pressure is important for optical sensing as motion artifacts and different contact pressure can affect optical sensing data.

Figure 10:
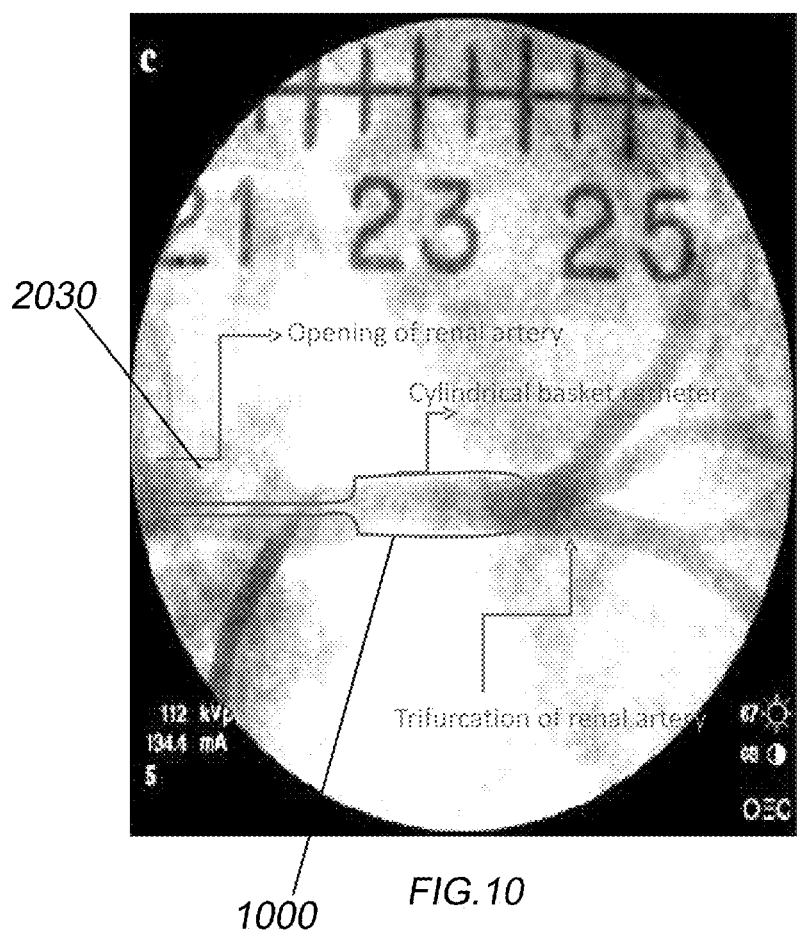
FIG. 10 shows a basket catheter used for renal denervation where the shape of the basket is rectangular or cylindrical, to conform to the tubular structure of the renal artery.

In a preferred embodiment of a basket catheter used for renal denervation, the shape of the basket is rectangular, to conform to the tubular structure of the renal artery 2020 (FIG. 10). For renal denervation, the size of the basket typically ranges from 2 mm to 6 mm in diameter and has a longer flat, linear segment (FIG. 2). The size of the basket can range from 2 mm to 70 mm in diameter. Length of each of the splines 1020 may range from 45 mm to 70 mm from the distal end of the basket where it attaches to the soft atraumatic cap 1030 to the proximal end. In a preferred embodiment, 10 holes are drilled into each arm or spline with the spacing of each of the holes being 760 micrometers from each other. In this preferred embodiment, each of the splines of the basket contain 10 apertures 1040 for allowing light from the illuminating optic fiber to illuminate tissue and the receiving optic fiber to receive light from the tissue. The diameter of the holes is 300 micrometer. The holes can have a 300 micrometer ball lens (as manufactured by DSI) to collimate and focus the returning light from the tissue to the receiving optic fiber wherein the ball lens is bonded to the hole by epoxy.

Figure 11:
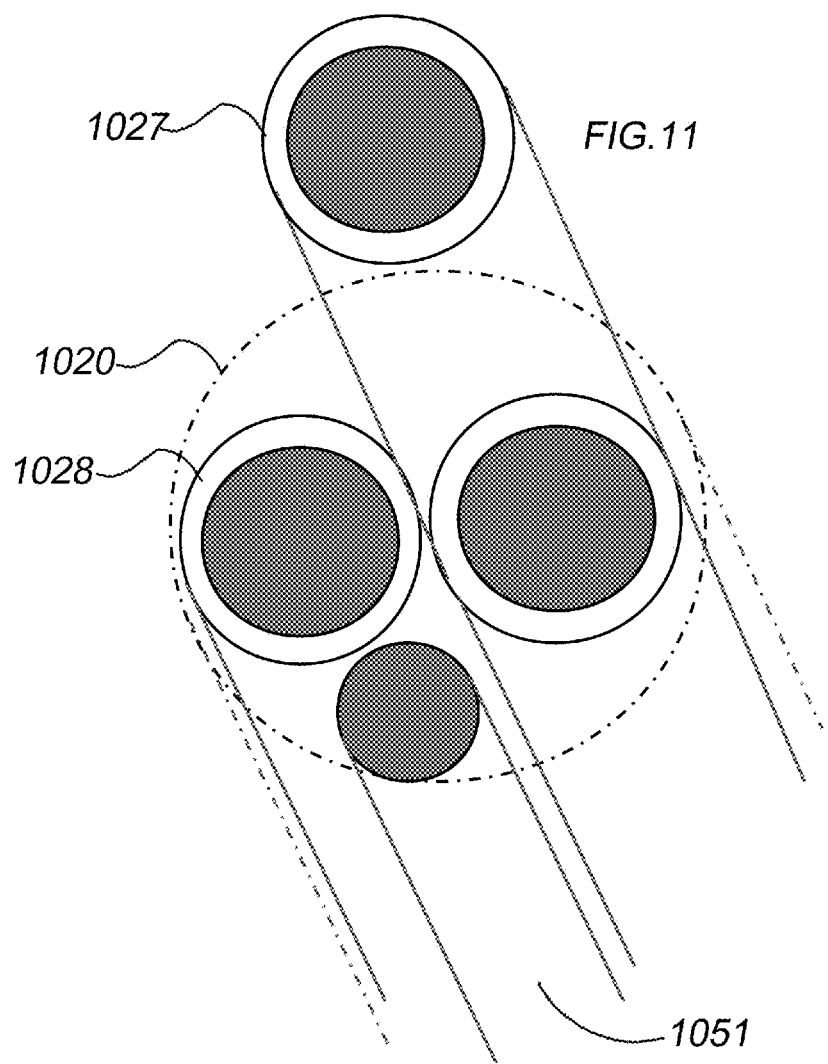
FIG. 11 shows a copper wire (50 to 100 micrometers in diameter) positioned on the inside wall of the spline to connect to the electrode.

An energy application element integrated into the catheter 1000 wherein energy application element consists of electrodes 1050 for applying energy to the inner wall of the heart. The electrodes are connected to energy source via electrical connections for providing electrical energy to the inner wall of the heart. The electrical connections are preferably wires located within the catheter. The 2 distal most holes are enclosed by electrode. Electrodes of a platinum-iridium alloy are mounted to the arms with cyanoacrylate or other adhesive beads. Each electrode carries a thermocouple, preferably a copper-constantan wire junction welded to the internal surface of the electrode. Each electrode, and any included thermocouple is attached to one or more wires to form wire bundle, which travels proximally and is attached to an electrical port on the proximal end of the ablation catheter. A copper wire (50 to 100 micrometers in diameter) runs on the inside wall of the spline to connect to the electrode. (FIG. 11). Each of the electrodes is attached via connecting wires and one or more connectors such as a conduit to an energy delivery apparatus, preferably an RF energy delivery unit, which is also attached to a patch electrode but preferably a conductive pad attached to the back of the patient. The energy delivery unit is configured to deliver RF energy in monopolar, bipolar or combination monopolar-bipolar energy delivery modes, simultaneously or sequentially with or without "off" or no energy delivered time duration.

Figure 12:
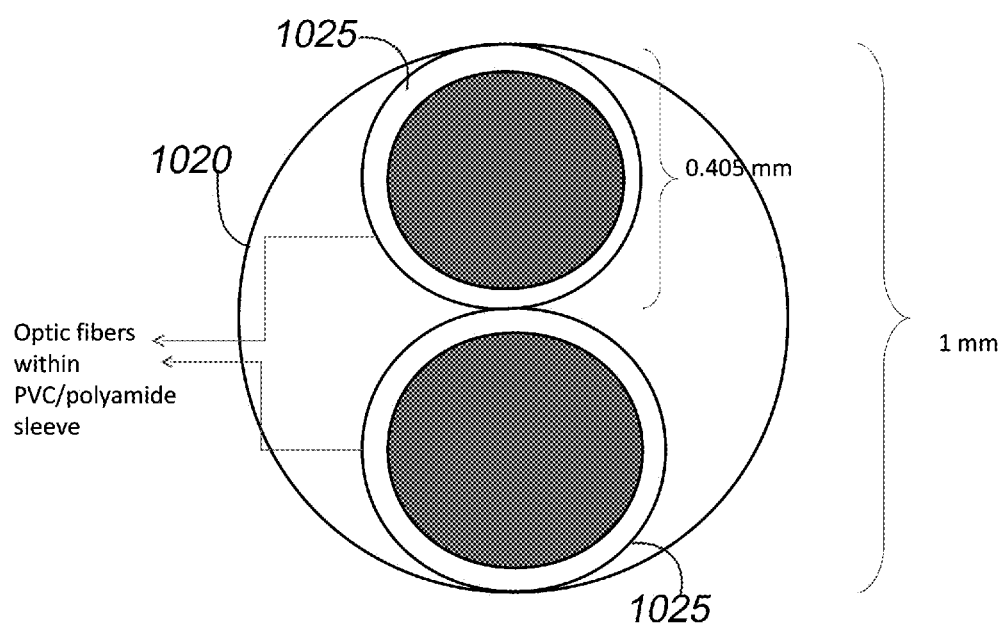
FIG. 12 shows that within hollow tube of each of the arms or splines, optic fibers are placed on top of each other.

In a preferred embodiment, the energy delivery unit is configured to provide electrical mapping of the tissue that is contacted by one or more electrodes integral to the basket. Alternatively, a separate mapping unit such as a MEMS gyroscope 1080 may be used, preferably attached to the catheter simultaneous with attachment to the energy delivery unit (FIGS. 8 and 9), in which case, copper wire 1081 also runs to the MEMS gyroscope The catheter of the present invention has an optical sensor 1010 integrated into it possessing a light emitting means and light receiving means. The optical sensor is adapted to generate optical sensing data depending on the received light. Light emitting and receiving means of the optical sensor comprise optic fibers. Illuminating optic fibers 1028 are connected to a light source such as a laser and the optic fibers guide the light to the tissue. The collection fibers 1027 are preferably connected to a spectrophotometer for generating optic spectra of the tissue wherein the invention is adapted to determine the characteristics of the tissue for example transmurality, of the ablation lesion depending on the characteristics of the optic spectra. A plurality of optic fibers are enclosed within each of the arms or splines 1020. One manufacturer of suitable optic fibers is (Polymicro, Ariz.). The optic fibers are multimode fibers and are 200 micrometers in diameter and have a numerical aperture of 0.22. Within a hollow tube of each of the arms or splines, the optic fibers are placed on top of each other (FIG. 12). The optic fibers can be covered or coated with PVC or polyamide to prevent crosstalk between the fibers.

Figure 13:
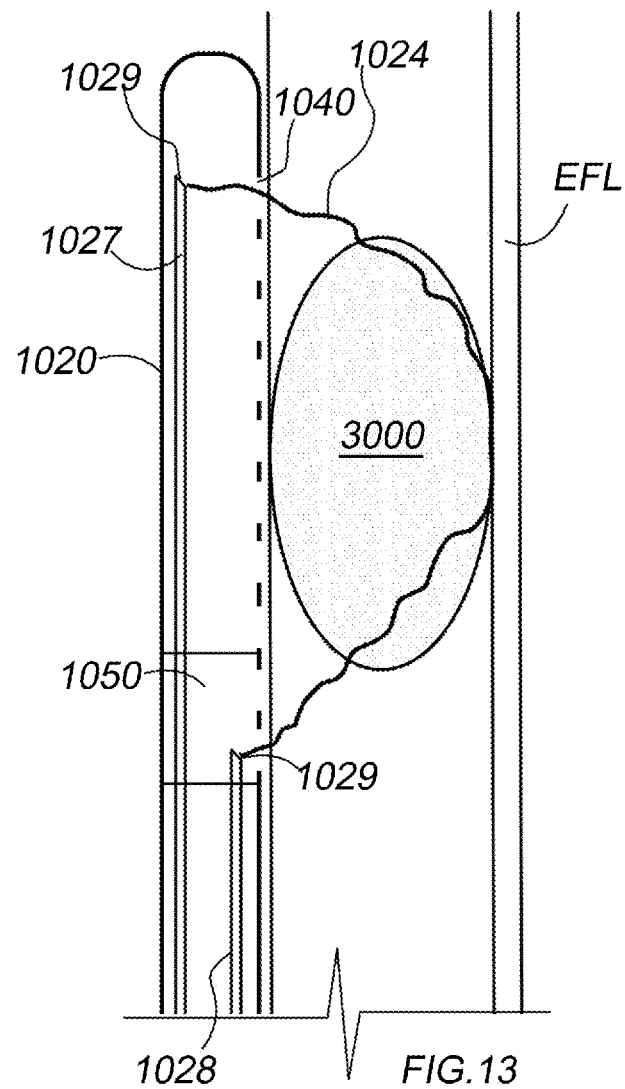
FIG. 13 depicts an example of atrial fibrillation ablation wherein an illuminating optic fiber is situated below the receiving optic fiber and is located proximal to the receiving fiber.

In cases of atrial fibrillation ablation for example, the illuminating optic fiber is situated below the receiving optic fiber and is located proximal to the receiving fiber. The illuminating optic fiber can be movable/translatable or fixed through application of cement (e.g., Norland 93, Norland Products) to the inner wall of the hollow tube of the arm or spline (FIG. 13).

Figure 14:
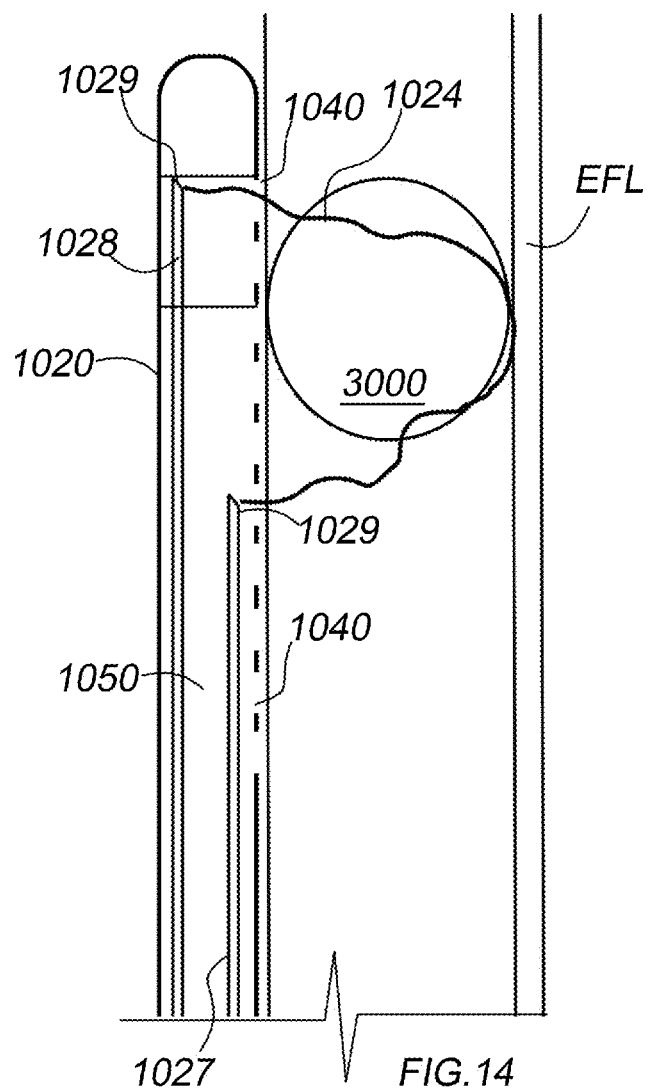
FIG. 14 depicts an example of renal denervation wherein an illuminating optic fiber is situated above the receiving fiber and is distal to the illuminating fiber.
Figure 15:
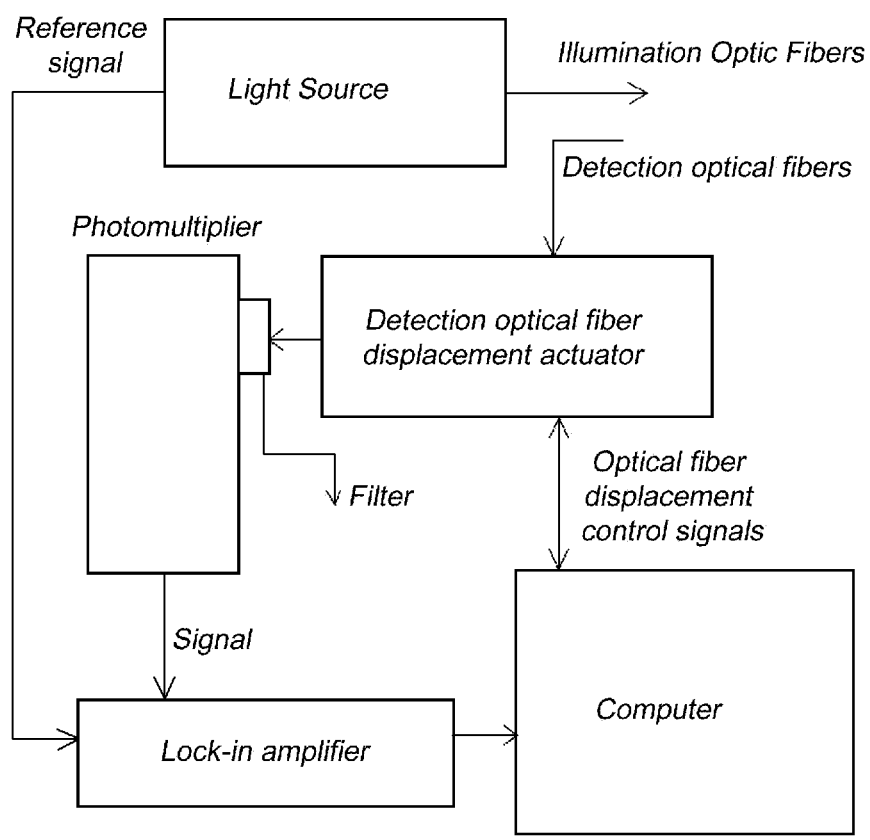
FIG. 15 is a schematic view depicting components of a system of one embodiment according to the present invention.

For renal denervation, the illuminating optic fiber is situated above the receiving fiber and is distal to the illuminating fiber (FIG. 14). The receiving optic fiber is not fixed but movable, and can be adapted to achieve a linear and rotational scan of the tissue by translating the optic fiber through a range of a linear distance between 2 to 20 mm and a rotation of between 10 to 60 degrees respectively. The driving force for the scan is provided by a linear/rotational galvanometer (FIG. 15). The translation provided by the linear galvanometer is transmitted to the tip by a polytetrafluoroethylene coated polyimide tube (Microlumen, Tampa, Fla.) containing the receiving optical fibers (FIG. 11).

In another embodiment, the galvanometer can also rotate the receiving and illuminating optic fibers to scan unablated areas on either side of the ablated area to provide an assessment of the area ablated. Both the illuminating and receiving optical fibers are adapted to illuminate the inner wall of the heart in a sideward looking direction. Light is coupled out from an optical fiber in a certain angle; e.g., 43 degrees, by polishing a slanted distal end on the respective optical fiber and by coating the surface at the slanted end with a metallic layer. Both the receiving and illuminating optic fibers each comprises a core and a cladding. On the polished slanted end surface of the optical fiber, a metallic coating is provided for forming a mirror 1029. The metallic coating can be, for example, a layer of approximately 100 nm of silver on a chromium adhesion promoter layer of approximately 5 nm. The light from the illuminating optic fiber is guided along the light path such that it is reflected by the mirror in a sideward looking direction. Light travelling back from the tissue at the receiving optic fiber similarly passes through the apertures into the distal end of the fiber and is reflected by the mirror back along the axis of the optic fiber. The returning light from the tissue may be collimated by a ball lens into the slanted end of the receiving optic fiber. The apertures can also be adapted for providing irrigation.

The present invention comprises an irrigation control unit being connected with the irrigation openings via an irrigation tube in order to allow the user to control irrigation of the cardiac tissue.

Setting Appropriate End Points for Ablation

1) Atrial Fibrillation Ablation

As tissue is undergoing heat denaturation for example by ablation, optical properties changes. Beauvoit et al reported that the mitochondrial compartment is the primary cause of light scattering. Thomsen et al. (US), hereinafter Thomsen, observed disruption of mitochondria into coarse granules, and discerned small aggregates resulting from denaturation of fibrillar contractile proteins and other cytoplasmic constituents. Based on their observations, Thomsen proposed that these thermally induced morphological changes are the physical cause of the increased rat myocardial tissue scattering observed with thermal coagulation.

By monitoring changes in these scattering optical properties, one can monitor the progress of the ablation. Optical properties commonly used to monitor the progress of ablation can be the scattering, absorption or reflectance. Reflectance can be an effective parameter to monitor the progress of ablation. Reflectance however, is a composite of the changes in absorption and scattering that is occurring as the ablation process continues. Monitoring the progress of ablation can also be confounded by the differing absorption properties of the different layers of tissues that are present in the tissue to be ablated. Furthermore, as the ablation process continues, blood leakage, tissue edema and tissue shrinkage can lead to dynamic changes in scattering and absorption properties which can confound the monitoring process. For example, tissue swelling and edema can occur after 500 seconds. One must therefore account for these aforementioned factors in order to be able to use reflectance to monitor the ablation process accurately. The reflectance signal is invariant to increased absorption at 800 nm. We can therefore probe ablated tissue based on measurement of the ratio between the reflectance signal at two wavelengths, for example one wavelength around the wavelength of interest (ranging from 400-2500 nm) and one around 800 nm. Normalized reflectance values are therefore obtained by obtaining a ratio of the reflectance at a particular wavelength to the reflectance at 800 nm. This ratio will allow the cancelling out of absorbance. Normalized reflectance will be used to monitor the ablation process in real time by tracking the rate of change of the normalized reflectance.

As ablation is being carried out, conductive heating and thermal diffusion through tissue leads to temperature elevation and the tissue temperature rises. This leads to the changes in the size and/or location of the optical scattering centers like the mitochondria due to disruption of mitochondria into coarse granules, and denaturation of fibrillar contractile proteins and other cytoplasmic constituents resulting in the formation of small aggregates that leads to an increase in the normalized reflectance. When ablation is started, there may be a lag phase of between 1 to 4 seconds (which may represent the time it takes for conductive heating and thermal diffusion through tissue) before there is a rise in the normalized reflectance. A steady rise in normalized reflectance is followed by a plateau where there is no change in the normalized reflectance, at which point the tissue is considered 100% denatured at that depth. Changes in normalized reflectance during the early time course of the ablation are fitted to the curve to the exponential function $1-\exp(-t/r)$, By modeling the above reaction on the Arrhenius equation for thermal denaturation, one can obtain the rate constant for the reaction which is equivalent to the slope of the curve at the point where 63% of the tissue is denatured. Referring to Fig. A, The reaction defined by the exponential function $1-\exp(-t/r)$, r is the rate constant of the denaturation reaction and is the value of the normalized reflectance when 63 percent of the tissue is denatured.

The Arrhenius equation for thermal damage is given by:

$$\Omega(\tau) = \int_0^\tau A e^{\left[\frac{-E_a}{RT(t)}\right]} dt$$

Where omega is the damage integral and is the logarithm of the ratio of the original concentration of native tissue to the remaining native tissue state at time torque, A is a frequency factor ($s^{-1}$), the total heating time (s), E. an activation energy barrier (J.mole$^{-1}$), R the universal gas constant, 8.3143 (J.mole$^{-1}$K$^{-1}$) and T the absolute temperature (K). The damage integral is therefore an indication of the percentage of proteins that have undergone denaturation. The damage integral is given by the rate of change of normalized reflectance. There is a critical temperature for which the damage integral is 1, that is 100% of tissue would have undergone denaturation for a given duration. For myocardial tissue, this critical temperature is 60 degrees Celsius. Accordingly, the Arrhenius equation predicts that for a given temperature 100% of tissue will be denatured for a given duration of exposure. For a series of lesions created at different temperatures but resulting in equivalent damage, a linear fit would yield AE/R as the slope, and $-\ln(A)$ as the intercept The Arrhenius model predictions for tissue damage is then compared to histological results, for example, nitroblue tetrazolium staining of ablated tissue as a marker of transmurality of the lesion, where 100% denaturation is equivalent to 100% transmurality Ex vivo and in vivo experiments are performed where the rate constant associated with a range of tissue temperature from 45 to 75 degrees Celsius (as determined by a thermocouple embedded in the tissue) and 100% transmurality (as determined by histology using NBT to assess for non viability of tissue) will be determined and stored in the memory of the invention.

The optimal rate constant associated with a tissue temperature of 60 degrees Celsius which will ensure 100% transmurality (as determined with histology using NBT to assess for non viability of tissue) within an ablation time of between 10 to 60 seconds will be determined from the ex vivo and in vitro experiments and will be stored in the memory of the invention. At the point where 100% tissue denaturation occurs, there is no further change in the reflectance properties of tissue observable as a plateau (the rate of change of normalized reflectance is zero). Therefore, by monitoring ablation process in real time, one can determine precisely the moment the tissue is denatured.

The point at which 100% tissue denaturation occurs leading to the plateau is time sensitive. There is a late phase after about 300 to 500 seconds where edema, blood leakage and tissue shrinkage will occur which can lead to changes in the normalized reflectance. Immediately at the time point where the plateau is reached, the illuminating and receiving optic fibers are scanned rotationally by the galvanometer from side to side, to determine the area of the ablated region at the surface. For determining the optical spectra, the optical sensor can illuminate the inner wall of the heart with light having different wavelengths, wherein the optical spectra are generated by using the spectrometer. Alternatively, the optical sensor can be adapted to illuminate the inner wall of the heart with different wavelengths temporally consecutively such that the optical fibers for receiving light from the inner wall of the heart receive light from substantially only one wavelength. The wavelength of interest may range from 400 nm to 2500 nm. For example, a wavelength of 2060 nm wherein a shift to a lower wavelength of 2056 nm corresponding to protein unfolding and protein denaturation from thermal energy application can be selected to discriminate between ablated and non ablated muscle tissue. The receiving optic fiber is rotated until the NIR spectra for non ablated tissue is discerned whereby the angle of rotation with the distance travelled gives an indication of the area ablated. Information obtained in the foregoing steps can be integrated with depth information to give a 3D representation of volume of ablated tissue, and is compared against histological and also spectroscopic assessments of volume of NBT dye staining.

By incorporating the measurement of the changes in normalized reflectance with respect to time into Arrhenius equation for thermal damage, the present invention offers the advantage that the plateau where the rate of change of normalized reflectance is zero can be registered sensitively at an earlier time frame/window (20 to 80 seconds) before edema, blood leakage and tissue shrinkage sets in (300 to 500 seconds) and therefore avoids the confounding influence of these factors on tissue optical properties.

Ex vivo and in vivo experiments determine the lag phase r which is the rate constant (or slope) for that reaction at that a particular temperature and the time to the plateau which will ensure 100% transmurality as based on NBT staining of tissue. Accordingly, there is an optimal lag phase, slope and time to plateau or is what we require to get complete lesion before tissue edema sets in and prevents the achievement of an effective ablation lesion. Stored rate constants of various energy and power settings (and the corresponding temperature) correlating with different times to plateaus, the lag phase associated with different pathological assessments showing different degrees of transmurality will be stored in the memory of the invention and used to guide ablation.

In cases where the operator is using too low of a power setting, there will be a significant deviation from the Arrhenius model and the algorithm can operate to shut off the power to prevent the operator from delivering an ineffective lesion or the algorithm can increase the power to get the operator back onto the curve (the right rate constant) and back onto the right track Based on the data accumulated in ex vivo and in vivo experiments, the invention's incorporated algorithm will be able to take the operator's power settings, lag phase and rate constant, compare it against the data in stored memory and allow the operator to calculate the percentage of denatured tissue in real time; i.e., 10%, 20% 50% etc., and tell the operator when he is done. This can be displayed on a user interface display unit. Because the measurements of normalized reflectance are performed as a function of time and depth, an M mode image can be generated that will provide a visualization of the thermal process. Using data from ex vivo and in vivo experiments, the depth information obtained from the spatially offset diffuse reflectance is compared against the histological data. This data is then integrated with data about the area of the ablation lesion at the surface to generate a 3D representation of the lesion which can be generated in real time.

The invention is also adapted to translate the receiving optic fiber as the ablation process is occurring wherein the initial position of the receiving optic fiber before ablation is carried out is located close to the illuminating fiber. As the ablation starts, the receiving optic fiber is translated away from the illuminating optic fiber. The distance between the illuminating and receiving optic fiber corresponds to the depth at which the photons have traveled and represents the depth of the muscle layer the optical sensor is relaying optical sensing data.

The galvanometer is programmed to track the duration of the ablation process (according to the rate constant and the time to the plateau data from in vivo and ex vivo experiments,) in the position for between 20-60 seconds until the plateau is obtained signifying that the muscle layer is denatured at this depth. By performing these measurements as a function of time and depth, M-mode images that provide a visualization of the thermal therapy process can be generated. The depth-localized intensity of the signal magnitude fluctuations is mapped according to a color bar. The maximum amplitude of the reflectance signal is plotted against time in an "M-mode image" The M-mode image is formed by mapping the reflectance signals to the indicated color space.

Determination of the Scattering and Absorption Coefficients from Spatially Offset Diffuse Reflectance Spectroscopy The present invention is further adapted to determine the kind of tissue or the composition of tissue. Optical spectra assigned to different types of tissues for example, fat, nerve, muscle, collagen, water are stored in the memory wherein the present invention is adapted to determine the respective kind of tissue or the composition of tissue by comparing the stored optical spectra with actually measured optical spectra. For determining the optical spectra, the optical sensor can illuminate the inner wall of the heart with light having different wavelengths, wherein the optical spectra are generated by using the spectrometer.

Alternatively, as described in the foregoing exemplary embodiment above under the section "Setting appropriate end points for ablation", the optical sensor can be adapted to illuminate the inner wall of the heart with different wavelengths temporally consecutively such that the optical fibers for receiving light from the inner wall of the heart receive light from substantially only one wavelength. In this situation, a spectrometer may not be needed but a photodetector that is sensitive to the respective wavelength. Therefore, the output of the optical fibers, which have received the light from the inner wall of the heart can be detected by a photodiode for generating a detector signal and the detector signal can be processed in accordance with an algorithm as will be described below.

The present invention uses spatially offset diffuse reflectance spectroscopy to collect reflectance spectra. It is advantageous to extract scattering and absorption coefficients from reflectance data obtained by SODRP. In order to extract absorption and scattering properties from reflectance measurements, spatially resolved intensities need to be obtained. Embodiments according to the present invention are adapted to measure the diffusely reflected light intensity at the surface of the tissue at different distances from the small illuminated surface spot. For tissue, the separation distances are in the range of between 2 to 20 mm. Therefore, the optical properties are derived from reflectance profiles measured at 10 source detector separated locations. Embodiments according to the present invention use a scanning approach with a side deflected illumination fiber and collection fiber that can be translated axially. The excitation light enters the probe via an optical fiber and is focused on the tissue surface near the end of the probe with the aluminized mirror surface on the polished angled surface of the distal end of the optic fiber. The intensity of the diffusely reflected light at the surface at different distances from the excitation spot is probed by displacing the movable optical fiber along the probe in such a way as to measure the light passing through the holes one after the other (counting the number of maxima in the measured diffuse reflectance curve), automatically gives the radial distance from the illumination spot along the surface, as the position of each hole is known. The fiber of the detection assembly then guides the light to a photomultiplier, the signal of which is amplified using a lock-in technique. A monochromator is inserted between fiber end and photomultiplier to avoid possibly important contributions from autofluorescence. The logarithm of the observed signal I (arbitrary units) is plotted against distance along the surface between excitation source and probing point. This data is then fitted to an analytic expression, which is based on diffusion theory. From the radial dependence of the diffusely reflected light intensity at the surface of the organ concerned, the tissue optical parameters may be extracted using the Groenhuis model.

The present invention can be adapted to use the algorithm to exact the tissue optical parameters, the scattering and absorption coefficients as disclosed in "Clinical optical dose measurement for PDT: Invasive and non-invasive techniques" by R Bays et al., SPIE Vol. 1525 Future Trends in Biomedical Applications of Lasers (1991), pages 397 to 408.

The present invention, using the algorithm described above can therefore determine the scattering coefficients and the absorption coefficients of different tissue chromophores like fat, water, muscle, collagen and nerves.

The present invention can also be adapted to discriminate differences in optical spectra by making use of a principal components analysis as disclosed in "Partial Least-Squares Methods for Spectral Analyses. 1. Relation to Other Quantitative Calibration Methods and the Extraction of Qualitative Information by David M Haaland al., Analytical Chemistry, vol. 60, no. 11 pages 1193 to 1202, June 1988, which is herewith incorporated by reference in its entirety. The principal component analysis allows classification of differences in optical spectra and, thus allows discrimination between tissues, in particular, between fat and muscle, between muscle and collagen, between fat and nerves and between ablated and non ablated tissue.

The present invention can also be adapted to discriminate between areas of heart muscle tissue infiltrated with fibrosis and areas with no fibrosis. In this embodiment, a bigger sized basket (for example 50 mm in diameter) is placed in the left atrium so that the basket approximates the endocardial surface of the left atrium.

The receiving optic fiber is scanned along the length of the spline in an axial direction and also rotationally in a side to side manner. As the receiving optic fiber is scanned along the surface of the tissue, it is able to distinguish for example, between areas of fibrosis (collagen) and muscle, fat and muscle, nerve and fat, muscle and fat.

The present invention is adapted to localize the depth of the fibrosis, fat, nerve and muscle with the algorithm described above that is adapted for spatially offset diffuse reflectance spectroscopy. The areas and location of interest, or example fibrosis, fat, and nerve can be tagged with the localization unit that is adapted to provide (x,y and z coordinates) of the area of interest, with a color scale denoting the concentration of fibrosis correlated with intensity of the optical parameter (for example, reflectance, scattering or absorption coefficient).

Before Ablation is Started, the Thickness of the Muscle Tissue Layer to be Ablated is Determined As mentioned previously, the present invention can be adapted to distinguish between fat and muscle to determine the depth at which ablation should be carried out by comparing an actually measured optical spectrum with stored optical spectra which are assigned to fat or muscle tissue.

In atrial fibrillation ablation, the adventitial fat layer represents the boundary beyond which the ablation should not be carried out, in order to avoid damage to the esophagus which lies beyond the adventitial fat layer of the left atrium.

The present invention can take advantage of the different optical properties of fat and muscle to limit the ablation before the fat layer to prevent collateral damage. The NIR spectra for fat tissue and for muscle tissue and for nerves is stored in the memory of the invention. In order to compare an actually measured optical spectrum with stored optical spectra, the present invention is preferentially adapted to use a similarity measure like a correlation or a sum of squared differences.

At the beginning of the ablation procedure, the illumination optic fiber is fired and the receiving optic fiber is scanned along the tissue to probe the deepest depth of the tissue until it registers the NIR signature of fat. This represents the deepest adventitial layer of fatty beyond which the ablation should not proceed. This is also the layer where critical structures like the phrenic nerve, adjacent to the right superior pulmonary vein are located. If the initial scanning process registers the NIR signature of nerve over the location of the right superior pulmonary vein, an alternative site may be targeted for ablation to prevent injury to the phrenic nerve. The depth at which the fatty adventitial layer is recorded at for example 5 mm. The spatial offset is then adjusted until the NIR signature of muscle is recorded. The muscle layer of the left atrium lies superficial to the fatty adventitial layer. So the depth of this muscle layer will be for example 4 mm. Ablation is then carried out. As discussed above, as the ablation is carried out, change in reflectance occurs. This change in reflectance will be normalized to get a ratio which will cancel out the effects of absorbance. This change in reflectance with respect to time can be fit to an exponential function which is modeled on the Arrhenius equation for thermal denaturation. The Arrhenius equation can predict a 100% transmurality (ie denatured tissue) for a particular tissue temperature (for example 60 degrees Celsius) held for a particular duration (for example 20 seconds). This particular set of conditions is associated with a thermal denaturation exponential curve with a rate constant that is given by the slope of the curve whereby 63% of the tissue has been denatured.

Ex vivo and in vitro experiments are performed with a thermocouple embedded into the target tissue to record the tissue temperature during ablation with a series of tissues temperatures recorded for different power settings with the tissues stained with NBT (or TTC) to determine the amount of viable tissue and therefore the extent of transmurality. Thus the exponential curve with the rate constant associated with a tissue temperature of 60 degrees Celsius and 100% transmurality and the duration required to achieve 100% transmurality is stored in the memory of the invention.

During an ablation procedure, an automated algorithm will reference this stored value with the current parameters of the thermal denaturation of ablation process and the power can be adjusted or titrated to approximate the stored value. When the exponential curve reaches a plateau, signifying 100% denaturation, the ablation process is terminated to avoid carrying the ablation process beyond into the adventitial fat layer and causing collateral damage. By way of a non-limiting example, the following represents a preferred algorithm for atrial fibrillation ablation: Traseptal catherization→Steerable sheath guided into pulmonary vein→Steerable sheath withdrawn→Basket expands to preformed shape→Basket withdrawn until it abuts tightly against the opening of the pulmonary vein with the radiopaque markers on the electrode signifying the desired position of the electrode at the os→illumination optic fiber is fired→Receiving optic fiber is translated by galvanometer→NIR spectra is compared with NIR spectra of fat stored in memory→Epicardial fat layer identified→Further scanning and/or rotation of the basket is performed until NIR for nerve is identified→Ablation is performed→Rate of change of normalized reflectance is followed as an exponential curve and the lag phase, the slope of the curve of the current reaction is compared against the reaction where 100% transmurality was obtained at a temperature of 60 degrees Celsius over a duration of 40 seconds→If the slope is less than the one stored in memory, computer algorithm then commands the energy delivery unit to increase the power until the slope matches the one for the ideal reaction rate stored in memory.

Renal Denervation

With current ablation devices for carrying out renal denervation, there is no end point to serve as a target for ablation. This can lead to application of too much power for too long a duration, leading to collateral damage. Using OCT, investigators have recorded thrombus formation and even dissection of the renal artery. The present invention can provide an endpoint for ablation for locating the depth where the renal sympathetic nerves are located using the NIR signature for nerves to track it. Once the depth of the nerves is located, for example at 4 mm, ablation is carried out. The rate constant for the thermal denaturation of nervous tissue is determined experimentally and used to guide the ablation process as described in the atrial fibrillation process. By way of a non-limiting example, the following represents a preferred algorithm for renal denervation: Femoral artery access→Steerable sheath guided into renal artery with flouroscopy→Steerable sheath withdrawn→Basket expands to preformed shape→Basket withdrawn until it abuts tightly against the renal artery with the radiopaque markers on the electrode signifying the desired position of the electrode just before the trifurcation of the renal artery→illumination optic fiber is fired→Receiving optic is translated by galvanometer→NIR spectra is compared with NIR spectra of fat stored in memory→Epicardial fat layer identified→Spatial offset at which this occurs is noted→Spatial offset adjusted to a lower offset until a more superficial layer of muscle just adjacent to the epicardial fat layer is identified→Ablation is perfomed→Rate of change of normalized reflectance is followed as an exponential curve and the lag phase, the slope of the curve of the current reaction is compared against the reaction where 100% transmurality was obtained at a temperature of 60 degrees Celsius over a duration of 40 seconds→If the slope is less than the one stored in memory, computer algorithm then commands the energy delivery unit to increase the power until the slope matches the one for the ideal reaction rate stored in memory.

Ventricular Tachycardia Ablation

For ventricular tachycardia ablation, the tissue to be ablated is thicker. Therefore a bigger spatial offset of 30 to 35 mm between the illuminating and receiving fibers will be required. This can be offset by being able to use a basket with a bigger diameter in the larger cavity of the ventricle. The optical sensor may further be adapted wherein the optical sensor is adapted to perform transmission spectroscopy by utilizing a plurality of basket catheters, wherein one basket catheter is placed in the pericardial space adjacent to a basket in the ventricular cavity wherein the optic fibers of the basket in the pericardial space are adapted to receive light from the illuminating fibers from the basket in the ventricular cavity.

Adaptation for Transmission Spectroscopy

The optical sensor may be adapted to perform transmission spectroscopy by utilizing a plurality of basket catheters, wherein one basket catheter is placed in an adjacent vein for example the coronary sinus vein to the left pulmonary veins wherein the optic fibers of the basket in the coronary sinus are adapted to receive light from the illuminating fibers from the basket in the left pulmonary veins.

The optical sensor may further be adapted to perform transmission spectroscopy by utilizing a plurality of basket catheters, wherein one basket catheter is placed in an adjacent vein for example the superior vena cava to the right pulmonary veins wherein the optic fibers of the basket in the superior vena cava are adapted to receive light from the illuminating fibers from the basket in the right pulmonary veins.

The optical sensor may further be adapted wherein the optical sensor is adapted to perform transmission spectroscopy by utilizing a plurality of basket catheters, wherein one basket catheter is placed in the pericardial space adjacent to a basket in the ventricular cavity wherein the optic fibers of the basket in the pericardial space are adapted to receive light from the illuminating fibers from the basket in the ventricular cavity.

4D Electroanatomic Mapping System

Embodiments of the current invention comprise a localization unit for localizing the ablation electrode. The localization unit (LU) comprises a MEMS gyroscope which is attached to the basket catheter, the Microsoft Kinect System and a fluoroscopy system. An Inertia Monitoring Unit (IMU) for inclusion in the proposed system includes motion sensors and a MEMS gyroscope incorporated at each of the electrodes on each of the arms or splines of the catheter which permits point by point localization of the catheter tip position and also improved stability of the catheter system The motion sensors may be any device capable of generating a signal that is indicative of the orientation or the rate of change of orientation of the sensor. The generated signal is preferably nearly proportional to the orientation or rate of change of the orientation of the sensor, but other dependencies are within the scope of the present invention. For example, a sensor may be a liquid level pendulous tilt sensor, a physical gyroscope, a solid-state gyroscope, an accelerometer, or a pair of proximity sensors arranged in a line and separated by a known distance. Lightweight accelerometers and lightweight body sway sensors, such as velocity transducers or sensors may also be used or included as part of the sensors. In addition, micro-electro-mechanical systems (MEMS) accelerometers, piezo-electric accelerometers, or other rotation and/or linear accelerometers can be used. In various embodiments of the present invention, a solid-state gyroscope is used with a liquid level tilt sensor. The liquid level tilt sensor may be used to correct for drift in the solid-state gyroscope.

A preferred embodiment of the invention includes a MEMS gyroscope because of its small size and low cost. A plurality of motion sensors and/or gyroscope(s) can monitor the position of the ablation catheter and feed signals to a processor. Preferably, the processor can perform a 3×3 matrix multiplication to computationally determine the roll, pitch and yaw. In a preferred embodiment, the motion processor then transmits the results from this computation to a holographic projection system, such as the Microsoft Kinect® system. The data from the computation will include x y and z coordinates which will be plotted into a holographic projection. In a preferred embodiment, at each point where x y and z coordinates are being generated, NIR, Raman, Fluorescence spectroscopy and OCT can be performed to collect depth data, which is the depth of the muscle tissue at a particular point. The processor will input the data from the Raman spectroscopy and calculate the depth data and use the depth data to translate the x y and z coordinates into an outer shell of the cardiac silhouette, creating a 4D image of the heart. At the beginning of the ablation procedure, fluoroscopy images will be taken in the right anterior oblique and the left anterior oblique views. The LAO and RAO views will be used to reconstruct a 3D image. A computer algorithm will then transform the 3D data into Cartesian coordinates (x,y and z data). The basket catheter is then placed in the pulmonary vein/renal artery and a fluoroscopy image is taken. This will serve as the initialization point for the MEMS gyroscope. The location of the eight electrodes is therefore registered by the gyroscope. The gyroscope requires no external reference once it is initialized. As ablation is carried out, depth information from spatially offset diffuse reflectance spectroscopy is integrated with the 3D data to generate a 4D image.

For example, at the beginning of the procedure, excitation of the tissue by the illumination optic fiber is performed and scanning is performed by the receiving optic fiber by translating the receiving optic fiber with a motorized linear galvanometer. The optical spectra obtained in real time is compared against stored optical spectra for fat. The correlation between actual depth of the epicardial fat layer and the spatial offset is determined histologically in ex vivo and in vivo experiments. The depth of the tissue at which the epicardial fat layer is detected relates to the spatial offset between the illuminating and the receiving optic fibers and this information is relayed to the gyroscope which registers this as depth information on the 3D Cartesian coordinate system. The spatial offset is then adjusted to detect the muscle layer that is just superficial to the epicardial fat layer again by comparing the optical spectra from the live on line data with stored optical spectra for muscle. The spatial offset at this depth is registered by the gyroscope. Ablation is then carried out.

Embodiments of the present invention are adapted to monitor the rate of change of reflectance as thermal denaturation is occurring. The rate of change of reflectance corresponds to the proportion of tissue that is being denatured. For a given temperature and a given rate constant, we can determine the time duration needed for 100% tissue denaturation to occur. Therefore, at each time point, the invention is adapted to indicate the proportion of tissue that has been denatured. This information can be calculated to give the depth. This depth info is sent to the gyroscope which then displays on the user interface the progression of the zone of damage as an M mode image. Once the first set of ablation is done, the location of the first set of 8 ablation points is registered by the gyroscope and the basket is rotated clockwise or counterclockwise to the ablation. Using the preferred configuration of 8 arms/splines, 2 or 3 rotations may be required to achieve a circumferential ablation around each pulmonary vein. Alternatively, in another embodiment, the invention may be adapted to provide a basket with between 16 to 20 splines to achieve circumferential ablation with "1 shot" ablation.

In view of the many possible embodiments to which the principles of the disclosed invention may be applied, it should be recognized that the illustrated embodiments are only preferred examples of the invention and should not be taken as limiting the scope of the invention. Therefore, this disclosure is intended to cover such alternatives, modifications, and equivalents as may be included in the spirit and scope of the description in view of the appended drawings and claims.

I claim:

1. An ablation catheter apparatus comprising:
    an elongated body member having a proximal end, and a distal end;
    a basket at the distal end, the basket comprising a plurality of radially expanding splines, the plurality of radially expanding splines including at least a first radially expanding spline, a second radially expanding spline, and a third radially expanding spline;
    a first electrode located on the first radially expanding spline, the first electrode configured to apply energy to tissue adjacent to the first radially expanding spline during an ablation procedure; and
    a second electrode located on the second radially expanding spline, the second electrode configured to apply energy to tissue adjacent to the second radially expanding spline during the ablation procedure;
    wherein at least one of the first radially expanding spline, the second radially expanding spline, or the third radially expanding spline includes:
    a first and a second aperture or aperture portion;
    a lumen;
    an optical emitting element inside the lumen configured to emit optical radiation through the first aperture and into adjacent tissue during the ablation procedure; and
    an optical receiving element inside the lumen configured to collect optical radiation through the first or the second aperture during the ablation procedure, the optical radiation indicating characteristics of adjacent tissue during the ablation procedure;
    wherein the optical receiving element and the optical emitting element are arranged such that there is a spatial offset between the optical receiving element and the optical emitting element along a longitudinal axis of the lumen.

2. The apparatus of claim 1 wherein the optical receiving element and the optical emitting element are configured for movement relative to one another along the longitudinal axis of the lumen such that the spatial offset between the optical receiving element and the optical emitting element is adjustable.

3. The apparatus of claim 2 wherein at least one of the optical receiving element or the optical emitting element is coupled to an actuating device, the actuating device being configured to cause the relative movement between the optical receiving element and the optical emitting element.

4. The apparatus of claim 3 wherein the actuating device is a linear actuator, or a rotational actuator.

5. The apparatus of claim 1, wherein the optical receiving element is connected to a processing element configured to process the optical radiation collected by the optical receiving element using spatially offset diffuse reflectance spectroscopy.

6. The apparatus of claim 5, wherein the processing element is configured to generate an optical spectra of the optical radiation collected by the optical receiving element.

7. The apparatus of claim 6, wherein the processing element is configured to compare the generated optical spectra of the optical radiation collected by the optical receiving element to a reference optical spectra for at least one of following tissue types: fat, nerve, muscle, or collagen.

8. The apparatus of claim 7, wherein the processing element is configured to determine that adjacent tissue is at least one of the following tissue types: fat, nerve, muscle, or collagen based at least on the comparison between the generated optical spectra and the reference optical spectra.

9. The apparatus of claim 6, wherein the processing element is configured to compare the generated optical spectra of the optical radiation collected by the optical receiving element to a reference optical spectra for tissue fluid.

10. The apparatus of claim 9, wherein the processing element is configured to determine that adjacent tissue contains tissue fluid based at least on the comparison between the generated optical spectra and the reference optical spectra.

11. The apparatus of claim 5, wherein the optical receiving element and the optical emitting element are configured for movement relative to one another along the longitudinal axis of the lumen such that the spatial offset between the optical receiving element and the optical emitting element is adjustable.

12. The apparatus of claim 5, wherein the processing element is configured to automatically calculate the rate of thermal denaturation of the tissue adjacent to the plurality of radially expanding splines.

13. The apparatus of claim 12, wherein the processing element is configured to extract a rate constant for the rate of thermal denaturation when the tissue adjacent to plurality of radially expanding splines is sixty three percent denatured.

14. The apparatus of claim 1, wherein the spatial offset between the optical receiving element and the optical emitting element has a magnitude such that the optical receiving elements collects optical radiation from at least a 5 mm tissue depth.

15. The apparatus of claim 1, wherein the optical emitting element and the optical receiving element are configured such that the optical receiving element collect near-infrared signatures from muscle tissue of at least 5 mm depth, the near-infrared signatures representing the extent of fibrosis within the muscle tissue.

16. The apparatus of claim 1, wherein the optical receiving element is connected to a processing element configured to process the optical radiation collected by the optical receiving element using at least one of the following techniques:
near-infrared spectroscopy, Raman spectroscopy, reflectance spectroscopy, optical coherence tomography, or birefringence.

17. The apparatus of claim 1, wherein a diameter of the deformable basket is equal to at least a vessel diameter of either a pulmonary vein or a renal artery such that the deformable basket is configured to abut an inner vessel surface of either the pulmonary vein or the renal artery.

18. The apparatus of claim 1, wherein a diameter of the deformable basket is equal to at least a diameter of a heart chamber such that the deformable basket is configured to approximate an endocardial surface of the heart chamber.

19. The apparatus of claim 1, wherein the first aperture is located on the first electrode or the second electrode.

20. The apparatus of claim 1, wherein the ablation catheter is connected to an energy source configured to provide energy to the first and second electrodes such that the first electrode applies energy to tissue adjacent to the first radially expanding spline substantially simultaneously as the second electrode applies energy to tissue adjacent to the second radially expanding spline.

21. The apparatus of claim 1, wherein the ablation catheter is connected to an optical radiation source configured to provide optical radiation to a first, second, and third optical illuminating elements such that the first, second, and third optically illuminating elements substantially simultaneously emit optical radiation.

22. The apparatus of claim 1, comprising an irrigation control unit connected to an irrigation tube configured to provide irrigation to tissue adjacent to the plurality of radially expanding splines through the first or second aperture.

23. A method comprising:
placing a portion of an ablation catheter apparatus within a human vessel, wherein the ablation catheter apparatus comprises an elongated body member having a proximal end, and a distal end, a basket at the distal end of the elongated body member, and a sheath covering the elongated body member between the proximal end and the distal end, the portion placed within the human vessel including at least the basket and the sheath;
withdrawing the sheath from the distal end of the elongated body member towards the proximate end of the elongated body member;
in response to withdrawing the sheath, exposing the basket comprising a plurality of radially expanding splines, and one or more electrodes located on the plurality of radially expanding splines configured to apply energy to tissue adjacent to the plurality of radially expanding splines during an ablation procedure,
wherein at least one of the plurality of radially expanding splines includes:
a first and a second aperture or aperture portion;
a lumen;
an optical emitting element inside the lumen configured to emit optical radiation through the first aperture and into adjacent tissue during the ablation procedure; and an optical receiving element inside the lumen configured to collect optical radiation through the first or second aperture during the ablation procedure, the optical radiation indicating characteristics of adjacent tissue during the ablation procedure;

wherein the optical receiving element and the optical emitting element are arranged such that there is a spatial offset between the optical receiving element and the optical emitting element along a longitudinal axis of the lumen, applying energy to tissue adjacent the plurality of radially expanding splines using the one or more electrodes;

emitting optical radiation through the first aperture into adjacent tissue using the optical emitting element; and collecting optical radiation through the first or second aperture using the optical receiving element, the optical radiation indicating characteristics of the adjacent tissue.

24. The method of claim 23, comprising moving the optical receiving element along the longitudinal axis of the lumen relative to the optical emitting element, wherein the movement along the longitudinal axis adjusts the spatial offset between the optical receiving element and the optical emitting element.

25. The method of claim 24, wherein moving the optical receiving element comprises using an actuating device coupled to at least one of the optical receiving element or the optical emitting element.

26. The method of claim 25, wherein using the actuating device comprises using a linear actuator, or a rotational actuator.

27. The method of claim 23, comprising processing the optical radiation collected by the optical receiving element using spatially offset diffuse reflectance spectroscopy.

28. The method of claim 27, wherein processing the optical radiation collected by the optical receiving element comprises generating an optical spectra of the optical radiation collected by the optical receiving element.

29. The method of claim 28, wherein processing the optical radiation collected by the optical receiving element comprises comparing the generated optical spectra of the optical radiation collected by the optical receiving element to a reference optical spectra for at least one of following tissue types: fat, nerve, muscle, or collagen.

30. The method of claim 29, wherein processing the optical radiation collected by the optical receiving element comprises determining that adjacent tissue is at least one of the following tissue types: fat, nerve, muscle, collagen, or water based at least on the comparison between the generated optical spectra and the reference optical spectra.

31. The method of claim 28, wherein processing the optical radiation collected by the optical receiving element comprises comparing the generated optical spectra of the optical radiation collected by the optical receiving element to a reference optical spectra for tissue fluid.

32. The method of claim 31, wherein processing the optical radiation collected by the optical receiving element comprises determining that adjacent tissue contains tissue fluid based at least on the comparison between the generated optical spectra and the reference optical spectra.

33. The method of claim 27, comprising moving the optical receiving element along the longitudinal axis of the lumen relative to the optical emitting element, wherein the movement along the longitudinal axis adjusts the spatial offset between the optical receiving element and the optical emitting element.

34. The method of claim 27, wherein processing the optical radiation collected by the optical receiving element comprises automatically calculating the rate of thermal denaturation of the tissue adjacent to the plurality of radially expanding splines.

35. The method of claim 34, wherein processing the optical radiation collected by the optical receiving element comprises extracting a rate constant for the rate of thermal denaturation when the tissue adjacent to plurality of radially expanding splines is sixty three percent denatured.

36. The method of claim 23, wherein collecting the optical radiation comprises collecting optical radiation from at least a 5 mm tissue depth.

37. The method of claim 23, wherein collecting the optical radiation comprises collecting near-infrared signatures from muscle tissue of at least 5 mm depth, the near-infrared signatures representing the extent of fibrosis within the muscle tissue.

38. The method of claim 23, comprising processing the optical radiation collected by the optical receiving element using at least one of the following techniques: near-infrared spectroscopy, Raman spectroscopy, reflectance spectroscopy, optical coherence tomography, or birefringence.

39. The method of claim 23, wherein the basket includes a diameter equal to at least a vessel diameter of either a pulmonary vein or a renal artery, the method comprising abutting the basket to an inner vessel surface of either a pulmonary vein or a renal artery.

40. The method of claim 23, wherein the basket includes a diameter equal to at least a diameter of a heart chamber, the method comprising approximating the basket to an endocardial surface of the heart chamber.

41. The method of claim 23, wherein abutting the basket to the inner vessel surface comprises applying a constant contact pressure along the inner vessel surface.

42. The method of claim 23, wherein the first aperture is located on the first electrode or the second electrode.

43. The method of claim 23, wherein applying energy to tissue adjacent the plurality of radially expanding splines comprises applying energy to tissue adjacent to the first radially expanding spline using the first electrode substantially simultaneously to applying energy to tissue adjacent to the second radially expanding spline using the second electrode.

44. The apparatus of claim 23, wherein collecting optical radiation through the first or second aperture using the optical receiving element comprises collecting optical radiation from tissue adjacent to the first radially expanding spline using a first optical receiving element inside the lumen of the first radially expanding spline substantially simultaneously to collecting optical radiation from tissue adjacent to the second radially expanding spline using a second optical receiving element inside the lumen of the second radially expanding spline.

45. The method of claim 23, comprising providing irrigation to tissue adjacent to the plurality of radially expanding splines through the first or second aperture using an irrigation control unit connected to an irrigation tube.

* * * * *